US012630502B2

(12) United States Patent
Van Rijen et al.

(10) Patent No.: US 12,630,502 B2
(45) Date of Patent: May 19, 2026

(54) COMPOUNDS, COMPOSITIONS AND POLYMER FILMS

(71) Applicants: Fujifilm Manufacturing Europe B.V., Tilburg (NL); Fujifilm Corporation, Tokyo (JP)

(72) Inventors: Adrianus Jacobus Van Rijen, Tilburg (NL); Takeshi Narita, Tilburg (NL); Elisa Huerta Martinez, Tilburg (NL); Jacko Hessing, Tilburg (NL)

(73) Assignees: Fujifilm Manufacturing Europe B.V., Tilburg (NL); Fujifilm Corporation, Tokyo (JP)

( * ) Notice: Subject to any disclaimer, the term of this patent is extended or adjusted under 35 U.S.C. 154(b) by 565 days.

(21) Appl. No.: 18/041,887

(22) PCT Filed: Sep. 27, 2021

(86) PCT No.: PCT/EP2021/076439
§ 371 (c)(1),
(2) Date: Feb. 16, 2023

(87) PCT Pub. No.: WO2022/069385
PCT Pub. Date: Apr. 7, 2022

(65) Prior Publication Data

US 2023/0312463 A1 Oct. 5, 2023

(30) Foreign Application Priority Data

Sep. 30, 2020 (GB) ...................................... 2015440

(51) Int. Cl.

| | |
|---|---|
| ***C07C 311/15*** | (2006.01) |
| ***B01D 61/42*** | (2006.01) |
| ***B01D 69/12*** | (2006.01) |
| ***B01D 71/28*** | (2006.01) |
| ***B01J 39/20*** | (2006.01) |
| ***C08J 5/18*** | (2006.01) |

(52) U.S. Cl.
CPC .......... *C07C 311/15* (2013.01); *B01D 61/422* (2013.01); *B01D 69/1213* (2022.08); *B01D 71/283* (2022.08); *B01J 39/20* (2013.01); *C08J 5/18* (2013.01); *C08J 2381/10* (2013.01)

(58) Field of Classification Search
None
See application file for complete search history.

(56) References Cited

U.S. PATENT DOCUMENTS

2017/0233596 A1* 8/2017 Hatakeyama ........ H10K 85/141 252/500

FOREIGN PATENT DOCUMENTS

| | | | | |
|---|---|---|---|---|
| EP | 3031798 A1 | | 6/2016 | |
| EP | 3031798 B1 | * | 9/2017 | ........ H01M 10/0568 |
| JP | 2018043936 A | * | 3/2018 | |
| JP | 2019214608 A | | 12/2019 | |
| WO | 98/50349 A1 | | 11/1998 | |

* cited by examiner

*Primary Examiner* — Robert S Jones, Jr.
*Assistant Examiner* — Lily K Sloan
(74) *Attorney, Agent, or Firm* — Banner & Witcoff, Ltd.

(57) ABSTRACT

A polymer film obtainable by curing a composition comprising a compound of Formula (I) wherein: R' is vinyl, epoxy $C_{1-3}$-alkylenethiol: n has a value of 1 or 2; m has a value of 1, 2 or 3; $M'^+$ is a cation; wherein X is as defined in the claims; and wherein the molar fraction of the compound of Formula (I) in relation to all curable compounds in the composition is greater than 0.25. Also claimed are compositions, processes membranes and their uses.

(I)

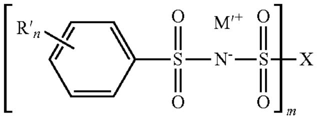

18 Claims, No Drawings

COMPOUNDS, COMPOSITIONS AND POLYMER FILMS

RELATED APPLICATIONS

This application is a National Stage Application under 35 U.S.C. 371 of co-pending PCT application PCT/EP2021/076439 designating the United States and filed Sep. 27, 2021; which claims the benefit of GB application number 2015440.7 and filed Sep. 30, 2020; each of which are hereby incorporated by reference in their entireties.

The present invention relates to compositions suitable for making polymer films, to polymer films, to cation exchange membranes, to bipolar membranes and to their preparation and use.

Ion exchange membranes are used in electrodialysis, reverse electrodialysis, electrolysis, diffusion dialysis and a number of other processes. Typically the transport of ions through the membranes occurs under the influence of a driving force such as an ion concentration gradient or, alternatively, an electrical potential gradient.

Ion exchange membranes are generally categorized as cation exchange membranes or anion exchange membranes, depending on their predominant charge. Cation exchange membranes comprise negatively charged groups that allow the passage of cations but reject anions, while anion exchange membranes comprise positively charged groups that allow the passage of anions but reject cations. A bipolar membrane has both a cationic layer and an anionic layer.

Some ion exchange membranes and bipolar membranes comprise a porous support which provides mechanical strength. Such membranes are often called "composite membranes" due to the presence of both an ionically-charged polymer which discriminates between oppositely charged ions and the porous support which provides mechanical strength.

Cation exchange membranes may be used for the treatment of aqueous solutions and other polar liquids, and for the generation of electricity.

Bipolar membranes may be used production of acids and bases from salt solutions e.g. for the recovery of hydrofluoric acid and nitric acid, for the separation and treatment of organic acids such as lactic acid and citric acid and for producing amino acids.

Electricity may be generated using reverse electrodialysis (RED) in which process standard ion exchange membranes or bipolar membranes may be used. Cation exchange membranes may also be used for the generation of hydrogen, e.g. in fuel cells and batteries.

Bipolar membranes can be prepared by many different methods. In U.S. Pat. Nos. 4,024,043 and 4,057,481 (both Dege et al.) single-film bipolar membranes are prepared from pre-swollen films containing a relatively large amount of an insoluble, cross-linked aromatic polymer on which highly dissociable cationic exchange groups are chemically bonded to the aromatic nuclei to a desired depth of the film from one side only; subsequently, highly dissociable anionic exchange groups are chemically bonded to the unreacted aromatic nuclei on the other side of the film.

In Japanese patent publication Nos. 78-158638 and 79-7196 (both Tokuyama Soda Co. Ltd.), bipolar membranes are prepared by partially covering a membrane with a cover film, sulphonating the surface of the membrane not in contact with the cover film to introduce cation exchange groups, exfoliating the cover film and introducing anion exchange groups on the exfoliated surface.

Bipolar membranes have also been prepared by bonding together an anion exchange film or membrane and a cation exchange film or membrane. The two monopolar membranes of opposite selectivity can be fused together with the application of heat and pressure to form a bipolar membrane. See, for example U.S. Pat. No. 3,372,101 to Kollsman wherein separate cation and anion membranes are bonded together in a hydraulic press at 150° C. at a pressure of 400 lb/sq. inch to form a two-ply bipolar membrane structure.

However, bipolar membranes formed in this way suffer the disadvantage of high electrical resistance produced by their fusion. Furthermore these membranes are prone to bubble or blister and they are operable for only short time periods at relatively low current densities.

The abovementioned disadvantages make the known bipolar membranes unattractive for commercial electrodialysis operations. There is a need for bipolar membranes which have good permselectivity and low electrical resistivity.

According a first aspect of the present invention there is provided a polymer film obtainable by curing a composition comprising a compound of Formula (I):

Formula (I)

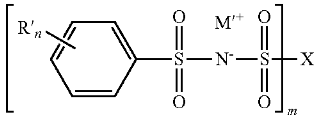

wherein:

R' is vinyl, epoxy or $C_{1-3}$-alkylenethiol:

n has a value of 1 or 2;

m has a value of 1, 2 or 3;

$M'^{+}$ is a cation;

wherein:

(i) when m and n both have a value of 1 then X is vinylphenyl or of Formula (II):

Formula (II)

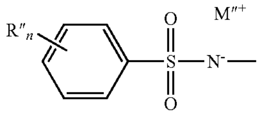

wherein in Formula (II):

R" is vinyl, epoxy or $C_{1-3}$-alkylenethiol;

$M''^{+}$ is a cation; and n in Formula (II) has a value of 1 or 2;

(ii) when m has a value of 2 or 3 then X is $C_{1-6}$-alkylene, —$C_{6-18}$-arylene, or $N(R''')_{(3-m)}$ wherein each R''' independently is H or $C_{1-4}$ alkyl; and (iii) when m has a value of 1 and n shown in Formula (I) has a value of 2 then X is of Formula (II) (as defined above) or $C_{1-6}$-alkyl, $C_{8-18}$-aryl, or $N(R''')_2$ wherein each R''' independently is H or $C_{1-4}$ alkyl;

wherein the molar fraction of the compound of Formula (I) in relation to all curable compounds in the composition is greater than 0.25. In this document (including its claims), the verb "comprise" and its conjugations is used in its non-limiting sense to mean that items following the word are included, but items not specifically mentioned are not excluded. In addition, reference to an element by the indefinite article "a" or "an" does not exclude the possibility that more than one of the elements is present, unless the context clearly requires that there be one and only one of the elements. The indefinite article "a" or "an" thus usually mean "at least one". The composition according to the second aspect of the present invention is often referred to as "the CEL composition".

Vinyl groups are of the formula $—CH═CH_2$.

Epoxy groups are of the formula $—C_2H_3O$.

$C_{1-3}$-alkylenethiol groups are of the formula $—C_{1-3}$-alkylene-SH.

$M'^+$ is preferably $H^+$, $Li^+$, $Na^+$, $K^+$ or $NL_4^+$ wherein each L independently is H or $C_{1-3}$-alkyl.

$M''^+$ is preferably $H^+$, $Li^+$, $Na^+$, $K^+$ or $NL_4^+$ wherein each L independently is H or $C_{1-3}$-alkyl.

Preferred $C_{6-18}$-arylene groups include phenylene ($C_6H_4$) and naphthylene ($C_{10}H_6$) groups and may be optionally substituted.

Preferred $C_{6-18}$-aryl groups include phenyl ($C_6H_5$) and naphthyl ($C_{10}H_7$) groups and may be optionally substituted.

In a preferred embodiment n is 1 and m is 2. In this embodiment R' and R" are preferably vinyl.

Preferred vinylphenyl groups are of the formula $—C_6H_4—CH═CH_2$.

Typically the composition comprises a compound of Formula (I) and further ingredients.

It is particularly preferred that $M'^+$ and $M'^+$ are $Li^+$, because this leads to compounds having particularly good solubility in water and aqueous liquids.

Illustrative synthesis methods for the above compounds of Formula (I) can be found below in the examples section. Furthermore, many of the compounds of Formula (I) may be prepared by a process comprising the steps of:

(i) providing a benzenesulfonyl chloride compound;

(ii) reacting the sulfonyl chloride group of component (i) with a compound comprising a sulfonamide group to obtain the compound of Formula (I);

wherein at least one of component (i) and component (ii) comprises a vinyl group, an epoxy group or a thiol group.

Typically the vinyl group, epoxy group or thiol group is attached to a benzene ring of one of the components (i) and (ii). In a preferred embodiment the benzenesulfonyl chloride compound used in the process comprises one or more vinyl groups, more preferably one or two vinyl groups.

In one embodiment the composition further comprises a compound comprising one and only one polymerisable group and a bissulfonylimide ($—S_2—N^-—SO_2—$) group.

According a second aspect of the present invention there is provided a composition comprising the following components:

(a) the compound of Formula (I) as defined in relation to the first aspect of the present invention;

optionally (b) a compound comprising one and only one polymerisable group;

optionally (c) a solvent; and optionally (d) a radical initiator;

provided that the molar fraction of the compound of component (a) in relation to all curable components of the composition is greater than 0.25.

Preferably the composition comprises one, two or all three of components (b), (c) and (d).

Preferably the composition according to the second aspect of the present invention comprises:

(a) 20 to 80 wt % of component (a);

(b) 0 to 50 wt % of component (b);

(c) 10 to 50 wt % of component (c); and (d) 0 to 10 wt % of component (d);

provided that the molar fraction of the compound of component (a) in relation to all curable components of the composition is greater than 0.25.

The preferences for the compound of Formula (I) used in the composition are as described above in relation to the first aspect of the present invention.

Preferably, in some embodiments, the composition comprises 30 to 75 wt %, more preferably 40 to 70 wt %, of component (a).

Preferably the molar fraction of the component (a) of the composition in relation to all curable components of the composition is at least 0.30, more preferably at least 0.40, especially at least 0.50.

Component (b) may be obtained commercially or by methods known generically.

Preferably component (b) comprises an anionic group. Preferably component (b) comprises bissulfonylimide ($—SO_2—N^-—SO_2—$) group.

Preferably the composition comprises 0 to 40 wt %, most preferably 5 to 30 wt % of component (b).

Preferred polymerisable groups which may be present in component (b) include ethylenically unsaturated groups, especially (meth)acrylic groups and/or vinyl groups (e.g. vinyl ether groups, aromatic vinyl compounds, N-vinyl compounds and allyl groups).

Examples of suitable (meth)acrylic groups include acrylate ($H_2C═CHCO—$) groups, acrylamide ($H_2C═CHCONH—$) groups, methacrylate ($H_2C═C(CH_3)CO—$) groups and methacrylamide ($H_2C═C(CH_3)CONH—$) groups. Acrylic groups are preferred over methacrylic groups because acrylic groups are more reactive.

Preferred ethylenically unsaturated groups are free from ester groups because this can improve the stability and the pH tolerance of the resultant composition. Ethylenically unsaturated groups which are free from ester groups include vinyl groups.

As preferred examples of polymerisable groups there may be mentioned groups of the following formulae:

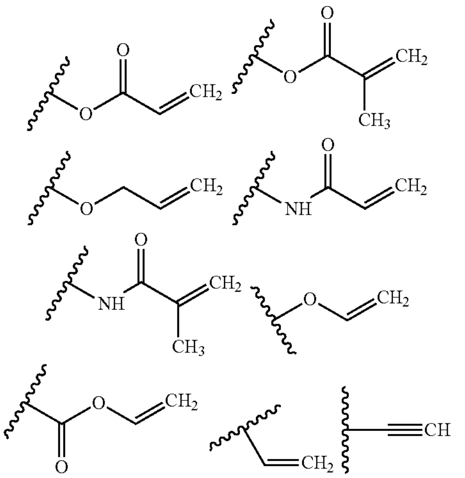

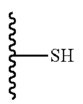

and

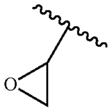

The preferred ethylenically unsaturated groups which may be present in component (b) are vinyl groups, e.g. in the form of (meth)acrylic, allylic or styrenic groups. Styrenic groups are preferred over (meth)acrylic groups as they increase the pH stability of the membranes to a range of 0 to 14, which is of special interest to bipolar membranes and cation exchange membranes for fuel cells.

Examples of a compounds having one and only one ethylenically unsaturated group which may be used as component (b) include the following compounds of Formula (MB-α), (AM-B) and Formula (III):

Formula (MB-α)

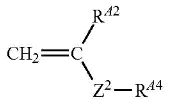

wherein in formula (MB-α), $R^{A2}$ represents a hydrogen atom or an alkyl group, $R^{A4}$ represents an organic group comprising a sulfo group in free acid or salt form and having no ethylenically unsaturated group; and $Z^2$ represents —NRa—, wherein Ra represents a hydrogen atom or an alkyl group preferably a hydrogen atom.

Examples of formula (MB-α) include:

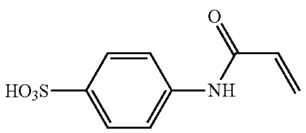

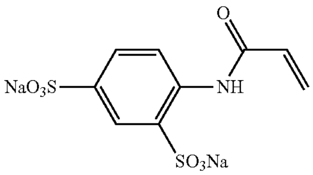

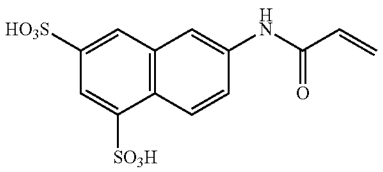

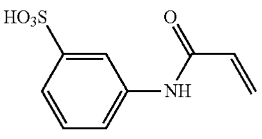

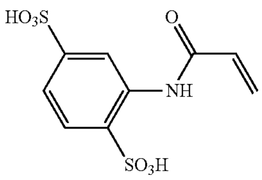

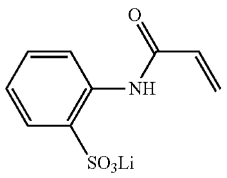

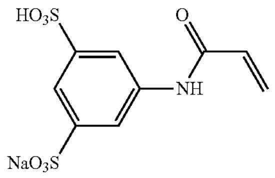

-continued

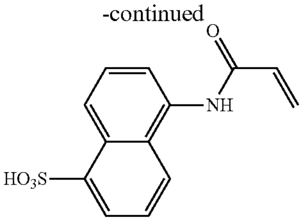

Synthesis methods can be found in e.g. US2015/0353696.

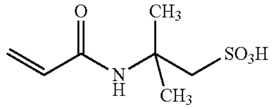

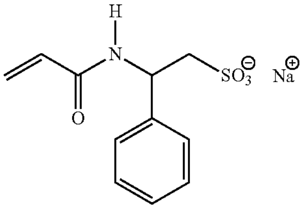

Synthesis methods can be found in e.g. US2016/0369017.

Formula (AM-B)

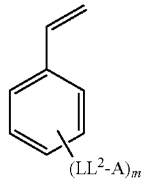

wherein in Formula (AM-B), $LL^2$ represents a single bond or a bivalent linking group; and A represents a sulfo group in free acid or salt form; and m represents 1 or 2.

Examples of formula (AM-B) include:

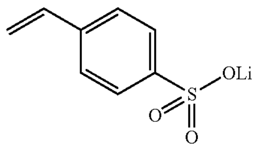

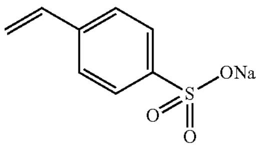

Such compounds are commercially available from e.g. Tosoh Chemicals and Sigma-Aldrich.

Formula (III)

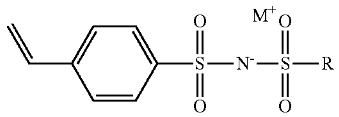

wherein

R is $C_1$-$C_4$ alkyl, $NH_2$, $C_6$-$C_{12}$ aryl; and $M^+$ is $H^+$, $Li^+$, $Na^+$, $K^+$, or $NL_4^+$ wherein L is H or $C_1$-$C_3$ alkyl.

Examples of Formula (III) include:

MM-Tf

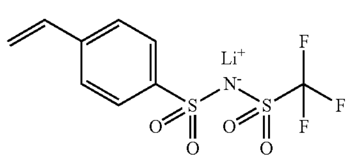

MM-A

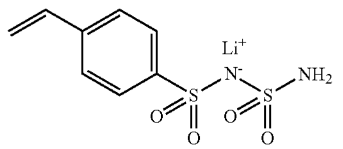

MM-P

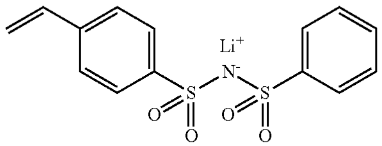

MM-M

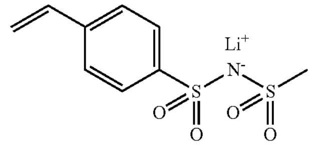

Synthesis methods for the above four compounds with the MM prefix are described in the Examples section below.

Preferably component (b) is chosen from the compounds according to Formula (AM-B) and/or Formula (III) because this can result in membranes having especially good stability in the pH range 0 to 14.

Preferably component (c) is an inert solvent. In other words, preferably component (c) does not react with any of the other components of the curable composition. In an embodiment the solvent preferably comprises water and optionally an organic solvent, especially where some or all of the organic solvent is water-miscible. The water is useful for dissolving component (a) and possibly also component (b) and the organic solvent is useful for dissolving any other organic components present in the composition.

Component (c) is useful for reducing the viscosity and/or surface tension of the composition. In some embodiments, the composition comprises 15 to 40 wt %, especially 20 to 38 wt %, of component (c).

Examples of inert solvents which may be used as component (c) include water, alcohol-based solvents, ether based solvents, amide-based solvents, ketone-based solvents, sulphoxide-based solvents, sulphone-based solvents, nitrile-based solvents and organic phosphorus based solvents. Examples of alcohol-based solvents which may be used as or in component (c) (especially in combination with water) include methanol, ethanol, isopropanol, n-butanol, ethylene glycol, propylene glycol, diethylene glycol, dipropylene glycol and mixtures comprising two or more thereof. In addition, preferred inert, organic solvents which may be used in component (c) include dimethyl sulphoxide, dimethyl imidazolidinone, sulpholane, N-methylpyrrolidone, dimethyl formamide, acetonitrile, acetone, 1,4-dioxane, 1,3-dioxolane, tetramethyl urea, hexamethyl phosphoramide, hexamethyl phosphorotriamide, pyridine, propionitrile, butanone, cyclohexanone, tetrahydrofuran, tetrahydropyran, 2-methyltetrahydrofuran, ethylene glycol diacetate, cyclopentylmethylether, methylethylketone, ethyl acetate, y-butyrolactone and mixtures comprising two or more thereof. Dimethyl sulphoxide, N-methyl pyrrolidone, dimethyl formamide, dimethyl imidazolidinone, sulpholane, acetone, cyclopentylmethylether, methylethylketone, acetonitrile, tetrahydrofuran, 2-methyltetrahydrofuran and mixtures comprising two or more thereof are preferable.

The composition preferably comprises 0 to 2 wt % of component (d). When it is intended to cure the composition thermally or using light (e.g. UV or visible light) the composition preferably comprises 0.001 to 2 wt %, especially 0.005 to 0.9 wt %, of component (d).

Examples of suitable thermal initiators which may be used as component (d) include 2,2'-azobis(2-methylpropionitrile) (AIBN), 4,4'-azobis(4-cyanovaleric acid), 2,2'-azobis(2,4-dimethyl valeronitrile), 2,2'-azobis(2-methylbutyronitrile), 1,1'-azobis(cyclohexane-1-carbonitrile), 2,2'-azobis(4-methoxy-2,4-dimethyl valeronitrile), dimethyl 2,2'-azobis(2-methylpropionate), 2,2'-azobis[N-(2-propenyl)-2-methylpropionamide, 1-[(1-cyano-1-methylethyl) azo]formamide, 2,2'-Azobis(N-butyl-2-methylpropionamide), 2,2'-Azobis(N-cyclohexyl-2-methylpropionamide), 2,2'-Azobis(2-methylpropionamidine) dihydrochloride, 2,2'-Azobis[2-(2-imidazolin-2-yl)propane]dihydrochloride, 2,2'-Azobis[2-(2-imidazolin-2-yl)propane]disulfate dihydrate, 2,2'-Azobis[N-(2-carboxyethyl)-2-methylpropionamidine] hydrate, 2,2'-Azobis{2-[1-(2-hydroxyethyl)-2-imidazolin-2-yl]propane} dihydrochloride, 2,2'-Azobis[2-(2-imidazolin-2-yl)propane], 2,2'-Azobis(1-imino-1-pyrrolidino-2-ethylpropane) dihydrochloride, 2,2'-Azobis{2-methyl-N-[1,1-bis (hydroxymethyl)-2-hydroxyethl]propionamide} and 2,2'-Azobis[2-methyl-N-(2-hydroxyethyl)propionamide].

Examples of suitable photoinitiators which may be included in the compositions as component (d) include aromatic ketones, acylphosphine compounds, aromatic onium salt compounds, organic peroxides, thio compounds, hexa-arylbiimidazole compounds, ketoxime ester compounds, borate compounds, azinium compounds, metallocene compounds, active ester compounds, compounds having a carbon halogen bond, and an alkyl amine compounds. Preferred examples of the aromatic ketones, the acylphosphine oxide compound, and the thio-compound include compounds having a benzophenone skeleton or a thioxanthone skeleton described in "RADIATION CURING IN POLYMER SCIENCE AND TECHNOLOGY", pp. 77-117 (1993). More preferred examples thereof include an alpha-thiobenzophenone compound described in JP1972-6416B (JP-S47-6416B), a benzoin ether compound described in JP1972-3981B (JP-S47-3981B), an alpha-substituted benzoin compound described in JP1972-22326B (JP-S47-22326B), a benzoin derivative described in JP1972-23664B (JP-S47-23664B), an aroylphosphonic acid ester described in JP1982-30704A (JP-S57-30704A), dialkoxybenzophenone described in JP1985-26483B (JP-S60-26483B), benzoin ethers described in JP1985-26403B (JP-S60-26403B) and JP1987-81345A (JPS62-81345A), alpha-amino benzophenones described in JP1989-34242B (JP H01-34242B), U.S. Pat. No. 4,318,791A, and EP0284561A1, p-di(dimethylaminobenzoyl)benzene described in JP1990-211452A (JP-H02-211452A), a thio substituted aromatic ketone described in JP1986-194062A (JPS61-194062A), an acylphosphine sulfide described in JP1990-9597B (JP-H02-9597B), an acylphosphine described in JP1990-9596B (JP-H02-9596B), thioxanthones described in JP1988-61950B (JP-S63-61950B), and coumarins described in JP1984-42864B (JP-S59-42864B). In addition, the photoinitiators described in JP2008-105379A and JP2009-114290A are also preferable. In addition, photoinitiators described in pp. 65 to 148 of "Ultraviolet Curing System" written by Kato Kiyomi (published by Research Center Co., Ltd., 1989) may be used.

Especially preferred photoinitiators include Norrish Type II photoinitiators having an absorption maximum at a wavelength longer than 380 nm, when measured in one or more of the following solvents at a temperature of 23° C.:water, ethanol and toluene. Examples include a xanthene, flavin, curcumin, porphyrin, anthraquinone, phenoxazine, camphorquinone, phenazine, acridine, phenothiazine, xanthone, thioxanthone, thioxanthene, acridone, flavone, coumarin, fluorenone, quinoline, quinolone, naphtaquinone, quinolinone, arylmethane, azo, benzophenone, carotenoid, cyanine, phtalocyanine, dipyrrin, squarine, stilbene, styryl, triazine or anthocyanin-derived photoinitiator.

According to a third aspect of the present invention there is provided a process for preparing a polymer film comprising curing a composition according to the second aspect of the present invention.

The preferences for the polymer film and composition used in the process of the third aspect of the present invention are as described herein in relation to the first aspect and second aspects of the present invention respectively.

The compositions may be cured to prepare films according to the first aspect of the present invention by any suitable process, including thermal curing, photocuring, electron beam (EB) radiation, gamma radiation, and combinations of the foregoing. Optionally, dual curing—defined as the combination of two of the above mentioned curing techniques—might be used. However the compositions are preferably cured by photocuring, e.g. by irradiating the compositions by ultraviolet of visible light and thereby causing the curable components present in the compositions to polymerise.

Preferably the polymer film according to the first aspect of the present invention further comprises a porous support. For example, the composition according to the second aspect of the present invention may further comprise a porous support and the process according to the thirst aspect of the present invention may be performed when the composition according to the first aspect of the present invention comprises a porous support.

The porous support is useful for providing mechanical strength to the polymer film and this is particularly useful when the polymer film is intended for use as a cation exchange membrane (CEM) or a bipolar membrane (BPM).

As examples of porous supports which may be used there may be mentioned woven and non-woven synthetic fabrics and extruded films. Examples include wetlaid and drylaid non-woven material, spunbond and meltblown fabrics and nanofiber webs made from, e.g. polyethylene, polypropylene, polyacrylonitrile, polyvinyl chloride, polyphenylenesulfide, polyester, polyamide, polyaryletherketones such as polyether ether ketone and copolymers thereof. Porous supports may also be porous membranes, e.g. polysulphone, polyethersulphone, polyphenylenesulphone, polyphenylenesulfide, polyimide, polyethermide, polyamide, polyamideimide, polyacrylonitrile, polycarbonate, polyacrylate, cellulose acetate, polypropylene, poly(4-methyl 1-pentene), polyinylidene fluoride, polytetrafluoroethylene, polyhexafluoropropylene and polychlorotrifluoroethylene membranes and derivatives thereof.

The porous support preferably has an average thickness of between 10 and 800 μm, more preferably between 15 and 300 μm, especially between 20 and 150 μm.

Preferably the porous support has a porosity of 30 and 95%. The porosity of the support may be determined by a porometer, e.g. a Porolux™ 1000 from IB-FT GmbH, Germany.

The porous support, when present, may be treated to modify its surface energy, e.g. to values above 45 mN/m, preferably above 55 mN/m. Suitable treatments include corona discharge treatment, plasma glow discharge treatment, flame treatment, ultraviolet light irradiation treatment, chemical treatment or the like, e.g. for the purpose of improving the wettability of and the adhesiveness to the porous support to the polymer film.

Commercially available porous supports are available from a number of sources, e.g. from Freudenberg Filtration Technologies (Novatexx materials), Lydall Performance Materials, Celgard LLC, APorous Inc., SWM (Conwed Plastics, DelStar Technologies), Teijin, Hirose, Mitsubishi Paper Mills Ltd and Sefar AG.

Preferably the support is a polymeric support. Preferably the support is a woven or non-woven synthetic fabric or an extruded film without covalently bound ionic groups.

According to fourth aspect of the present invention there is provided a bipolar membrane (BPM) comprising the polymer film according to the first aspect of the present invention.

Preferably the polymer film is a cation exchange membrane (CEM) or a cation exchange layer (CEL) of a bipolar membrane (BPM), preferably obtained by a process comprising curing a composition according to the second aspect of the present invention and/or by a process according to the third aspect of the present invention. Preferably the BPM further comprises an anion exchange layer (AEL).

Preferably the polymer film according to the first aspect of the present invention comprises a group of Formula (A):

Formula (A)

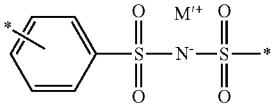

wherein is as hereinbefore defined.

In Formula (A) the asterisks indicate where the structural group covalently attaches to other groups in the polymer film (which may or may not be of Formula (A)).

In a preferred embodiment the polymer film according to the first aspect of the present invention is free from fluorine, e.g. free from perfluoro-groups. This preference arises for environmental reasons.

In a preferred process according to the third aspect of the present invention, the curable composition according to the second aspect of the present invention may be applied continuously to a moving (porous) support, preferably by means of a manufacturing unit comprising a curable composition application station, one or more irradiation source(s) for curing the composition, a membrane collecting station and a means for moving the support from the curable composition application station to the irradiation source(s) and to the membrane collecting station.

The curable composition application station may be located at an upstream position relative to the irradiation source(s) and the irradiation source(s) is/are located at an upstream position relative to the membrane collecting station.

Examples of suitable coating techniques for applying the curable composition according to the second aspect of the present invention to a (porous) support include slot die coating, slide coating, air knife coating, roller coating, screen-printing, and dipping. Depending on the used technique and the desired end specifications, it might be desirable to remove excess coating from the substrate by, for example, roll-to-roll squeeze, roll-to-blade or blade-to-roll squeeze, blade-to-blade squeeze or removal using coating bars. Curing by light is preferably done at a wavelength between 400 nm and 800 nm using a dose between 40 and 1500 $mJ/cm^{-2}$. In some cases additional drying might be needed for which temperatures between 40° C. and 200° C. could be employed.

The process according to the third aspect of the present invention may be used to prepare, for example, polymer films according to the first aspect of the present invention and BPMs according to the fourth aspect of the present invention in several ways, including multi-pass and single-pass processes. For example, in a two-pass process, each of a BPM's layers (e.g. the CEL and AEL) may be produced in separate steps. In the first step to make a first layer, an optionally pre-treated porous support may be impregnated with a first curable composition. To ensure a thin and pinhole-free membrane, the coating step is preferably followed by squeezing to remove air. The impregnated support may then be cured, yielding a layer hard enough to be handled in the coating machine, but still containing enough unreacted polymerisable groups to ensure good adhesion to the second layer. In the second step, a very similar process as for the first layer is employed: an optionally pre-treated porous support may be impregnated with a second curable composition and laminated to the first layer followed by squeezing-off excess composition and curing.

In an alternative method for making a BPM, the second layer may be coated on the first layer, followed by laminating an optionally pre-treated porous support at the side of the second curable composition whereby the second curable composition impregnates the porous support. The resulting laminate may be squeezed and cured to yield the BPM.

In the above described two-pass processes, either the first curable composition or the second curable composition is as defined in the second aspect of the present invention.

In a more preferred single-pass process for preparing a BPM, two optionally pre-treated porous supports are unwound and each is impregnated with a curable composition (e.g. simultaneously or consecutively), wherein one of the curable compositions is as defined in the second aspect of the present invention to give a CEL, and the other curable composition comprises at least one cationic curable monomer to provide an AEL. The two layers (CEL from the composition according to the second aspect of the present invention and the AEL from the other curable composition) are then laminated together and squeezed to remove air, followed by curing of the resulting laminate to yield the final BPM.

The efficiency of the BPM according to the fourth aspect of the present invention may be enhanced by enlarging the surface area between the AEL and the CEL, e.g. by physical treatment (roughening) or by other means.

In one embodiment, the BPM according to the fourth aspect of the present invention optionally comprises a catalyst, e.g. metal salts, metal oxides, organometallic compounds, monomers, polymers or co-polymers or salt, preferably at the interface of the BPM's CEL and AEL.

Suitable inorganic compounds or salts which may be used as a catalyst include cations selected from, for example, group 1 a through to group 4a, inclusive, together with the lanthanides and actinides, in the periodic table of elements, for example thorium, zirconium, iron, lanthanum, cobalt, cadmium, manganese, cerium, molybdenum, nickel, copper, chromium, ruthenium, rhodium, tin, titanium and indium and combinations comprising two or more of the foregoing. Suitable salts which may be used as a catalyst include anions such as tetraborate, metaborate, silicate, metasilicate, tungstate, chlorate, phosphate, sulfate, chromate, hydroxyl, carbonate, molybdate, chloroplatinate, chloropaladite, orthovandate, tellurate and others, or mixtures of the above.

Other examples of inorganic compounds or salts which may be used as a catalyst include, but are not limited to, $FeCl_3$, $FeCl_2$, $AlCl_3$, $MgCl_2$, $RuCl_3$, $CrCl_3$, $Fe(OH)_3$, $Al_2O_3$, NiO, $Zr(HPO_4)_2$, $MoS_2$, graphene oxide, Fe-polyvinyl alcohol complexes, polyvinyl alcohol (PVA), polyethylene glycol (PEG), polyethyleneimine (PEI), polyacrylic acid (PAA), co-polymer of acrylic acid and maleic anhydride (PAAMA) and hyperbranched aliphatic polyester and combinations comprising two or more of the foregoing.

When the polymer film according to the first aspect of the present invention is a CEM or CEL it preferably has a very high density as a result of being obtained from a composition according to the second aspect of the present invention having a molar fraction of component (a) in relation to all curable components of the composition of greater than 0.25, e.g. by ensuring that the composition comprises a low amount of component (c) (e.g. from 10 to 40 wt % of component (c)). Thus the present invention enables the production of polymer films (e.g. CEMs and BPMs) having a very high ion exchange capacity and therefore a high permselectivity (PS) and low electrical resistance (ER).

Preferably, the polymer film has an ER (for 0.5 M NaCl) of less than 5 $ohm\cdot cm^2$, more preferably less than 2.5 $ohm\cdot cm^2$.

It is preferred that component (b) of the composition comprises a compound of Formula (AM-B) and/or Formula (III) as defined above (including salts of the foregoing) because this can result in polymer films (e.g. CEMs and BPMs) having excellent pH stability in the range from 0 to 14.

Furthermore, the polymer films of the present invention, whether used as a CEM or as the CEL in a BPM, have low electrical resistance. As a result, the polymer films and BPMs according to the present invention can be used in bipolar electrodialysis to provide high voltages at low current densities. Thus when the BPMs of the present invention are used in bipolar electrodialysis processes for the production of acid and base they can provide low energy costs and/or high productivity.

In one embodiment the polymer film according to the first aspect of the present invention is preferably a BPM or a membrane which is convertible by hydrolysis to a BPM.

The anion exchange layer (AEL) of the BPM is preferably obtainable by curing a composition comprising a curable cationic compound (i.e. "the AEL composition"). Thus the AEL composition preferably comprises a curable cationic compound.

A preferred curable cationic compound comprises at least two ethylenically unsaturated groups, e.g. it is a compound of Formula (IV):

Formula (IV)

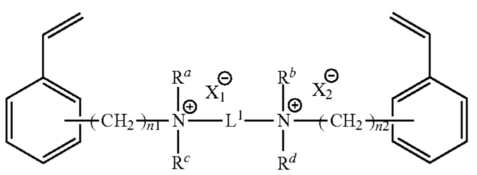

wherein:

$L^1$ is an alkylene group or an alkenylene group;

$R^a$, $R^b$, $R^c$, and $R^d$ are each independently an alkyl group or an aryl group, or $R^a$ and $R^b$, and/or $R^c$ and $R^d$ may, together with the atoms to which they are attached, form a ring;

n1 and n2 each independently represent an integer having a value of 1 to 10; and $X_1^-$ and $X_2^-$ each independently represent an anion.

$L^1$ is preferably ethylene ($CH_2CH_2$), propylene ($CH_2CH_2CH_2$), hexylene ($CH_2CH_2CH_2CH_2CH_2CH_2$) or vinylene ($CH{=}CH$).

When any of $R^a$, $R^b$, $R^c$, and $R^d$ is an alkyl group it is preferably a $C_{1-4}$-alkyl group, especially methyl.

When any of $R^a$, $R^b$, $R^c$, and $R^d$ is an aryl group it is preferably a $C_{6-10}$-aryl group, especially phenyl.

When $R^a$ and $R^b$, and/or $R^c$ and $R^d$, together with the atoms to which they are attached, form a ring, the ring is preferably a 5- or 6-membered ring.

The anions represented by $X_1^-$ and $X_2^-$ are preferably each independently halo, especially $Cl^-$.

Thus AEL composition preferably comprises the following ingredients:

(a2) a curable cationic compound comprising at least two ethylenically unsaturated groups;

optionally (b2) a compound comprising one and only one ethylenically unsaturated group;

optionally (c2) a solvent; and optionally (d2) a radical initiator.

Preferably the AEL composition comprises at least one, more preferably at least two, especially all three of components (b2), (c2) and (d2).

Examples of compounds of Formula (IV) include the following:

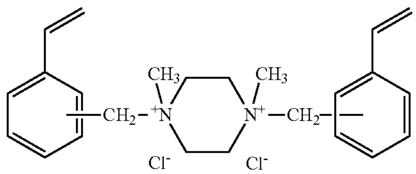

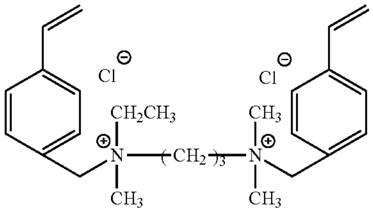

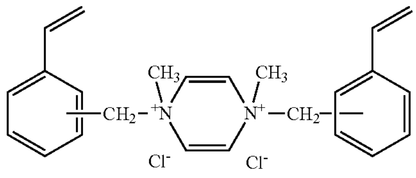

-continued

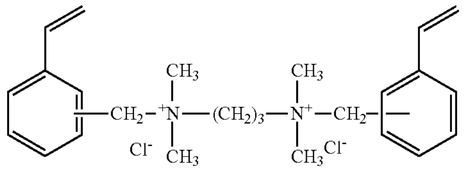

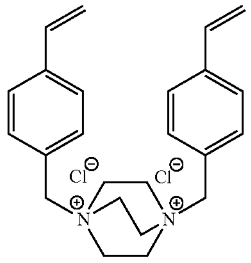

Synthesis methods for compounds of Formula (IV) can be found in, for example, EP3184558 and US2016/0001238.

The AEL composition preferably comprises 30 to 80 wt % of component (a2), more preferably between 40 and 70 wt % of component (a2).

Preferably the AEL_composition comprises:

(i) 30 to 80 wt % of component (a2);

(ii) 0 to 60 wt % of component (b2); and (iii) 10 to 40 wt % of component (c2).

Component (b2) preferably comprises an aromatic group.

Component (b2) preferably comprises a cationic group.

Examples of compounds which may be used as component (b2) of the AEL composition include the following:

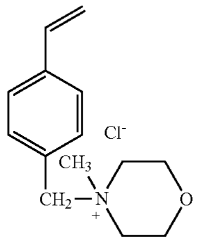

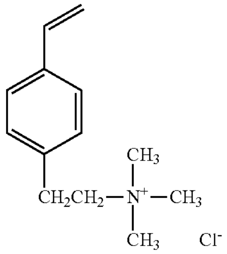

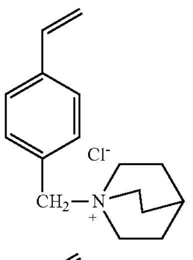

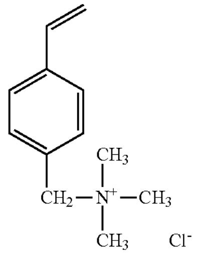

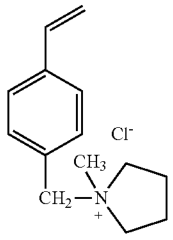

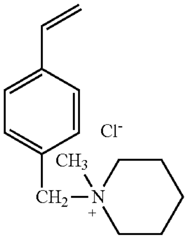

-continued

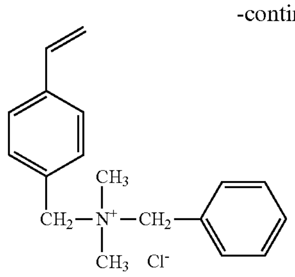

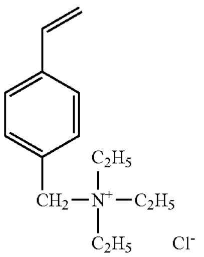

The above compounds may be prepared as described in, for example, US2016177006.

Preferably the molar ratio of component (a2) to component (b2) is from 9:1 to 1:4.

The AEL composition preferably comprises 0 to 45 wt %, more preferably 5 to 45 wt %, most preferably 10 to 40 wt % of component (b2).

Preferably component (c2) is an inert solvent. In other words, preferably component (c2) does not react with any of the other components of the AEL composition.

Component (c2) of the AEL composition preferably comprises water and optionally an organic solvent. Preferably some or all of the organic solvent is water-miscible. The water is useful for dissolving the compound of Formula (IV) and also component (b2), when present. The solvent is useful for reducing the viscosity and/or surface tension of the composition.

Examples of suitable solvents which may be used as component (c2) of the AEL composition include water, alcohol-based solvents, ether-based solvents, amide-based solvents, ketone-based solvents, sulfoxide-based solvents, sulfone-based solvents, nitrile-based solvents, organic phosphorus based solvents and mixtures comprising two or more thereof. Examples of alcohol-based solvents which may be used as or in component (c2) (especially in combination with water) include methanol, ethanol, isopropanol, n-butanol, ethylene glycol, propylene glycol, diethylene glycol, dipropylene glycol and mixtures comprising two or more thereof. In addition, preferred inert, organic solvents which may be used in component (c2) include dimethyl sulfoxide, dimethyl imidazolidinone, sulfolane, N-methylpyrrolidone, dimethyl formamide, acetonitrile, acetone, 1,4-dioxane, 1,3-dioxolane, tetramethyl urea, hexamethyl phosphoramide, hexamethyl phosphorotriamide, pyridine, propionitrile, butanone, cyclohexanone, tetrahydrofuran, tetrahydropyran, 2-methyltetrahydrofuran, ethylene glycol diacetate, cyclopentylmethylether, methylethylketone, ethyl acetate, y-butyrolactone and mixtures comprising two or more thereof. Dimethyl sulfoxide, N-methyl pyrrolidone, dimethyl formamide, dimethyl imidazolidinone, sulfolane, acetone, cyclopentylmethylether, methylethylketone, acetonitrile, tetrahydrofuran, 2-methyltetrahydrofuran and mixtures comprising two or more thereof are preferable.

In some embodiments, the AEL composition comprises 10 to 40 wt %, more preferably 10 to 35 wt %, most preferably 15 to 30 wt % of component (c2).

Examples of components (c2) to (d2) which may be included in the AEL composition used to form the AEL are as described above in relation to the CEL composition as components (c) and (d) respectively. However component (c2) of the AEL composition is preferably aqueous.

Component (d2) preferably is or comprises a thermal initiator, a photoinitiator or a combination thereof. Most preferably component (d) is or comprises a photoinitiator.

Examples of suitable photoinitiators which may be used as component (d2) of the AEL composition include those described above in relation to the CEL composition according to the second aspect of the present invention.

The AEL composition preferably comprises 0.001 to 2 wt % of component (d2), more preferably 0.005 to 0.9 wt %.

The AEL composition and the CEL composition optionally each independently further comprise a polymerization Inhibitor. A polymerization Inhibitor can be useful for making the composition stable during storage and use.

As the polymerization inhibitor, well-known polymerization inhibitors can be used. Examples thereof include phenol compounds, hydroquinone compounds, certain amine compounds, mercapto compounds, and nitroxyl radical compounds.

Examples of phenol compounds include hindered phenols (phenols having a t-butyl group in an ortho position, and representatively 2,6-di-t-butyl-4-methylphenol), and bisphenols. Specific examples of hydroquinone compounds include monomethyl ether hydroquinone. Specific examples of amine compounds include N-nitroso-N-phenyl hydroxylamine and N,N-diethylhydroxylamine. Specific examples of nitroxyl radical compounds include 4-hydroxy TEMPO (4-hydroxy-2,2,6,6-tetramethylpiperidine-1-oxyl free radical).

The AEL composition and the CEL composition optionally each independently further comprise two or more polymerisation inhibitors.

When the CEL composition or the AEL composition comprises a polymerization inhibitor the content is preferably 0.01 to 5 wt %, more preferably 0.01 to 1 wt %, and further preferably 0.01 to 0.5 wt %, relative to the total weight of the relevant composition.

The AEL composition and the CEL composition optionally each independently further comprise a surfactant, a polymer dispersing agent and/or a crater inhibitor.

In order to adjust film physical properties of the AEL composition and/or CEL composition, various polymer compounds may be included therein. Suitable polymer compounds include acrylic polymers, polyurethane resins, polyamide resins, polyester resins, epoxy resins, phenol resins, polycarbonate resins, polyvinyl butyral resins, polyvinyl formal resins, shellac, vinylic resins, acrylic resins, rubber-based resins, waxes, and natural resins and combinations of two or more of the foregoing.

The AEL composition and the CEL composition optionally each independently further comprise a surfactant, e.g. a nonionic surfactant, a cationic surfactant, an organic fluoro surfactant, or the like. Specific examples of surfactants include anionic surfactants (e.g. an alkylbenzene sulfonic acid salt, alkylnaphthalene sulfonic acid salts, higher fatty acid salts, sulfonic acid salts of higher fatty acid esters, sulfuric acid ester salts of higher alcohol ethers, sulfonic acid salts of higher alcohol ethers, alkylcarboxylic acid salts of higher alkylsulfone amides and alkylphosphoric acid salts) and non-ionic surfactants (e.g. poly(oxyethylene) alkyl ethers, poly(oxyethylene) alkyl phenyl ethers, poly (oxyethylene) fatty acid esters, sorbitan fatty acid esters, ethylene oxide adducts of acetylene glycol, ethylene oxide adducts of glycerin, and polyoxyethylene sorbitan fatty acid esters). Other examples suitable surfactants include amphoteric surfactants (e.g. alkyl betaines and amide betaines), silicone-based surfactants and a fluorine-based surfactant. The surfactant can be suitably selected from the surfactant known in the art or a derivative thereof.

The AEL composition and the CEL composition optionally each independently further comprise a polymer dispersant.

Specific examples of polymer dispersant include polyvinyl pyrrolidone, polyvinyl alcohol, polyvinyl methyl ether, polyethylene oxide, polyethylene glycol, polypropylene glycol and polyacryl amide. Among these, it is preferable to use polyvinyl pyrrolidone.

The AEL composition and the CEL composition optionally each independently further comprise a crater inhibitor (sometimes referred to as a surface conditioner), a levelling agent or a slipping agent to prevent unevenness on the CEM/CEL or AEL surface, examples of which include organomodified polysiloxanes (mixtures of polyether siloxane and polyether), polyether-modified polysiloxane copolymers and silicon-modified copolymers.

Examples of the commercially available surfactants which may be included in the AEL composition and/or the CEL composition include Tego Glide™ 432, Tego Glide™ 110, Tego Glide™ 130, Tego Glide™ 406, Tego Glide™ 410, Tego Glide™ 411, Tego Glide™ 415, Tego Glide™ 420, Tego Glide™ 435, Tego Glide™ 440, Tego Glide™ 450, Tego Glide™ 482, Tego Glide™ A115, Tego Glide™ B1484 and Tego Glide™ ZG400 (all are product names), manufactured by Evonik industries GmbH.

The AEL composition and the CEL composition preferably each independently comprise 0 to 10 wt %, more preferably 0 to 5 wt % and especially 1 to 2 wt % of crater inhibitor (relative to the total weight of the relevant composition).

As mentioned above, in a preferred embodiment the BPM according to the fourth aspect of the present invention comprises a catalyst. In one embodiment the AEL composition and/or the CEL composition further comprise a catalyst. Also it is possible to apply the catalyst (as a post-treatment step) to the AEL (e.g. before applying the CEL composition thereto) using, for example, (but not limited to), dipping, air knife coating, microroller coating, spraying, chemical (vapour) deposition) or physical (vapour) deposition. Examples of suitable catalysts are as described above.

When the AEL composition or the CEL composition comprises a catalyst, the amount of catalyst is preferably up to 5 wt %, e.g. 0.001 wt % to 1 wt %, relative to the weight of the relevant composition.

The BPM according to the fourth aspect of the present invention may be prepared by a process comprising the steps:

(i) applying the AEL composition to a support;
(ii) at least partly curing the AEL composition, thereby forming an anion exchange layer (AEL);
(iii) applying the CEL composition to the AEL; and
(iv) curing the CEL composition, thereby forming a cation exchange layer (CEL) on the AEL.

In step (ii) preferably the AEL composition is photocured, e.g. using ultraviolet light. Therefore preferably component (d2) of the AEL composition is or comprises a photoinitiator.

In step (ii), preferably the AEL composition is cured to such an extent that the resultant AEL can be processed in a curable composition application station while still comprising unreacted ethylenically unsaturated groups that are available for crosslinking to one or more components of the CEL composition.

In step (iv) the CEL composition is preferably cured thermally. Therefore preferably component (d) of the CEL composition is or comprises a thermal initiator.

A suitable temperature for curing the CEL composition is from 50 to 120° C., more preferably from 50 to 100° C., especially 60 to 85° C.

Thermal curing of the CEL composition typically takes from one minute to several hours.

Optionally the CEL composition is cured when it further comprises a porous support and is sandwiched between transparent foils to prevent evaporation of component (c), when present.

The CEL and AEL compositions are preferably applied in step (i) and (iii) in a continuous manner, preferably by means of a manufacturing unit comprising composition application stations, one or more curing stations comprising irradiation source(s) when a composition is photocurable, one or more curing stations comprising a one or more heat source(s) when a composition is thermally curable, a bipolar membrane collecting station and a means for moving the supports from the composition application stations to the curing station(s) and to the bipolar membrane collecting station.

The composition application stations may be located at an upstream position relative to the curing station(s) and the curing station(s) is/are located at an upstream position relative to the bipolar membrane collecting station.

Examples of application techniques include slot die coating, slide coating, air knife coating, roller coating, screen printing, and dipping. Depending on the used technique and the desired end specifications, it might be necessary to remove excess composition from the porous support by, for example, roll-to-roll squeeze, roll-to-blade or blade-to-roll squeeze, blade-to-blade squeeze or removal using coating bars.

Photocuring by ultraviolet or visible light is preferably performed at a wavelength between 100 nm and 800 nm, typically using a dose of light of between 40 and 1500 $mJ/cm^2$. Thermal curing is preferably performed at a temperature of between 20° C. and 100° C., e.g. for a period of 0.01 hour to 24 hours.

The performance of the BPMs according to the fourth aspect of the present invention may be characterized by means of an intensity versus voltage plot. For measuring this plot a six-compartment cell is preferably used. The $1^{st}$ electrode compartment preferably contains a platinum plate as cathode and is separated from the $2^{nd}$ compartment by a CEM (CMX from Astom). The electrode compartment is preferably filled with 0.5 M $Na_2SO_4$. Between the $2^{nd}$ and the $3^{rd}$ compartment a reference BPM (from Fumatech) is preferably present. Both the $2^{nd}$ and the $3^{rd}$ compartment preferably contain a 0.5 M NaCl solution. Between the $3^{rd}$ and $4^{th}$ compartment the BPM to be analyzed is placed. Between the $4^{th}$ and the $5^{th}$ compartment the same reference BPM is placed (from Fumatech) and between the $5^{th}$ and the $6^{th}$ compartment a CEM (CMX from Astom). Preferably the $4^{th}$ and $5^{th}$ compartments are also filled with a 0.5 M NaCl solution. The $6^{th}$ compartment preferably contains a platinum plate as anode and is an electrode compartment and contains 0.5 M $Na_2SO_4$.

By using the above six-compartment cell solutions of 0.5 M NaCl and $Na_2SO_4$ may be pumped through the respective compartments at a temperature of 25° C. and at an applied current density of 600 $A/m^2$. Bipolar voltages may be measured using a Harber-Luggin capillary placed at each side of the BPM to be analyzed.

The CEMs and the BPMs containing a cationic exchange layer (CEL) according to the present invention have good pH stability high permselectivity and low electrical resistance. As a result, the CEMs and BPMs according to the present invention can be used in bipolar electrodialysis to provide high voltages at low current densities. Thus when the BPMs of the present invention are used in bipolar electrodialysis processes for the production of acid and base they can provide low energy costs and/or high productivity.

EXAMPLES

In the following non-limiting Examples all parts and percentages are by weight unless specified otherwise.

TABLE 1

Ingredients

| Abbreviation | Component Type | Description |
|---|---|---|
| XL-B | (a) | Benzenesulphonamide, 4-ethenyl-N-[(4-ethenylphenyl)sulphonyl]-, lithium salt |
| 4OH-TEMPO | | 4-hydroxy-2,2,6,6-tetramethylpiperidin-1-oxyl, a polymerization inhibitor from Sigma-Aldrich |
| LiSS | | Styrene sulphonate, lithium salt from Tosoh Chemicals (A Comparative Example) |
| MM-Tf | | Benzenesulphonamide, 4-ethenyl-N-[(trifluoromethyl)sulphonyl]-, lithium salt (A Comparative Example) |
| MM-M | (b) | Benzenesulphonamide, 4-ethenyl-N-(methylsulphonyl)-, lithium salt |
| MM-A | (b) | Benzenesulphonamide, 4-ethenyl-N-(aminosulphonyl)-, lithium salt |
| MM-P | (b) | Benzenesulphonamide, 4-ethenyl-N-(phenylsulphonyl)-, lithium salt |
| XL-D | (a) | Benzenesulphonamide, 2,4-diethenyl-N-(methylsulphonyl)-, lithium salt |
| XL-2 | (a) | 1,3-[N-(ethenylphenylsulphonyl)benzene sulphonamide], dilithium salt |
| MeOH | (c) | Methanol from Sigma-Aldrich |
| IPA | (c) | Isopropyl alcohol from Sigma-Aldrich |
| MCH | (c) | Methylcyclohexane from Sigma-Aldrich |
| 1MP | (c) | 1-methyl pyrrole from Sigma-Aldrich |
| DMSO | (c) | Dimethylsulfoxide from Sigma-Aldrich |
| TEOA | (c) | Triethanolamine from Sigma-Aldrich |
| THF | | Tetrahydrofuran from Sigma-Aldrich |
| LiH | | Lithium hydride from Sigma-Aldrich |
| Celite ™ | | Celite ™ S, diatomaceous earth ($SiO_2$) from Sigma-Aldrich |
| DVBS-Na | | Divinylbenzenesulphonate, Sodium salt from Tosoh Chemicals |
| LAP | (d) | phenyl-2,4,6-trimethylbenzoylphosphinate, lithium salt from Sigma-Aldrich (a photoinitiator) |
| Na-AMPS | | Sodium salt of 2-acrylamideo-2-methylpropane sulfonic acid, 50 wt % in water from Sigma-Aldrich. (A Comparative Example) |
| M-11 | | Sodium 5-(prop-2-enoylamino)-2-[4-(prop-2-enoylamino)-2-sulfonato-phenyl]benzenesulfonate. Structure is shown below, preparation method was as described in EP2965803. |
| Omnirad ™ TPO-L | (d) | Ethyl(2,4,6-trimethylbenzoyl)-phenyl phosphinate, a photoinitiator from IGM Resins |
| Omnirad ™ 1173 | (d) | 2-hydroxy-2-methyl-1-phenylpropanone, a photoinitiator from IGM Resins |
| PP/PE Support | | A polypropylene/polyethylene porous support obtained under the name FO2223-10 from Freudenberg |
| PE support | | A non-woven polyethylene fabric obtained under the name Soluporfrom Lydall performance materials |

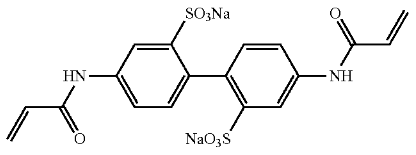

M-11

Inductively coupled plasma atomic emission spectroscopy (ICP-OES) was used to quantify the lithium content of the prepared compounds of Formula (I). The ICP-OES analyses were performed using a Thermo iCAP™ PRO XP ICP-OES apparatus from Thermo Fisher Scientific. A concentric nebulizer was used in conjunction with a Cyclonic spray chamber. Approximately 50 mg of each compound under test was dissolved in 50 $cm^3$ of Milli-Q water. The dissolved compounds were diluted 100 times, and acidified with 0.5% concentrated nitric acid containing Yttrium as internal standard. All samples were prepared and measured in duplicate. Results are expressed as g of Li per kg monomer.

The structures of the compounds of Formula (I) were confirmed by $^1$H-NMR using a Magritek Spincolve 60 Carbon (60 MHz, 4 scans) NMR spectrometer. Samples for analysis were prepared by dissolving 5 wt % of each compound of Formula (I) in DMSO-$d_6$.

Example structures of compounds of Formula (I):

XL-2

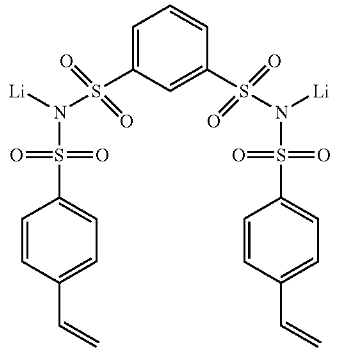

XL-D

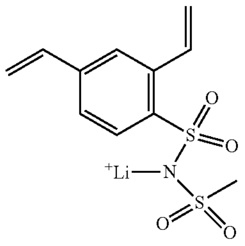

XL-B

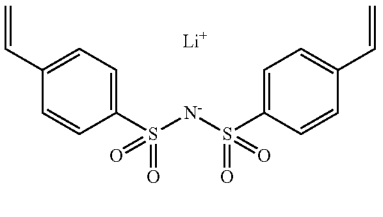

The purity of the compounds of Formula (I) was determined by HPLC-MS. A Waters ACQUITY UPLC System with 2D Technology was used. The UPLC was equipped with 2 pumps (BSM and QSM), FTN sample manager, column manager and a PDA detector (192 until 400 nm). The HPLC was equipped with a Waters Xbridge C8 5 μm 2.1*150 mm column, using 45° C. as working temperature. Additionally, the instrument was also equipped with Waters Q-TOF premier mass spectrometer with ESI and ESCi ionisation options. Dual detection mode was used to collect the chromatogram. The PDA detector collected signals at 245 nm. The mass detector was set in negative mode to detect anionic molecules. Samples containing compounds of Formula (I) were prepared as follows: 5 mg of the compounds of Formula (I) was dissolved in 50 ml Milli-Q water. The resultant solution was diluted 10 times with Milli-Q water and 10 μl volume was injected into the abovementioned HPLC-MS apparatus for analysis.

Table 2 shows the typical method employed to elute the samples of the compounds of Formula (I) indicated in Table 3. In Table 3, an overview of the retention times and molecular weights recorded for material identification is given

TABLE 2

HPLC method

| Time (min) | Flow Rate (ml/min) | Solvent 1 (%): water | Solvent 2 (%): MeOH |
|---|---|---|---|
| 0.0 | 0.6 | 95.0 | 5.0 |
| 1.0 | 0.6 | 95.0 | 5.0 |
| 30.0 | 0.6 | 0.0 | 100.0 |
| 34.1 | 0.6 | 95.0 | 5.0 |
| 40.0 | 0.6 | 95.0 | 5.0 |

TABLE 3

Identification of example materials and impurities.

| Compound | Exact mass (Daltons) | Mass observed (Daltons) | Retention time (min)* |
|---|---|---|---|
| LiSS | 190 | 183 | 12.2 |
| Na-DVBS | 232 | 209 | 19.5 |
| XL-2 | 580 | 573 | 17.5 |
| XL-B | 355 | 348 | 25.4 |
| XL-D | 293 | 286 | 20.2 |

*Retention times are indicative. Small shifts retention times were observed between samples depending on the sample's purity among other factors. CI-SS and CI-DVBS were converted into their sulphonic acids upon dissolution in water.

The solubility of the compounds of Formula (I) was determined visually or by UV-spectrometry. For each compound of Formula (I), three solutions were prepared at 40° C.: one solution at 30 wt %, one solution at 60 wt %, and one solution at 70 wt %. 500 ppm 4OH-TEMPO was included in all three solutions to prevent premature polymerisation. The solutions were kept in a water bath of 40° C. overnight and centrifuged prior inspection. UV spectra were recorded in a Cary™ 100 UV-visible spectrophotometer from Agilent Technologies using a 1 mm path length quartz cuvette.

Formula (I)

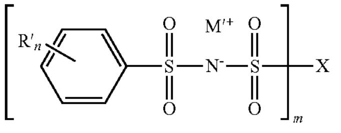

TABLE 4

Solubility in water of several compounds of Formula (I) and of a comparative compound (DVBS-Na)

Compounds of Formula (I)

| Name | R | n | m | X | M | Solubility in water at 40° C. (wt %) |
|---|---|---|---|---|---|---|
| XL-D | vinyl | 2 | 1 | methyl | Li | >70 |
| XL-B | vinyl | 1 | 1 | p-vinylphenyl | Li | 56 |
| XL-2 | vinyl | 1 | 2 | phenylene ($C_6H_4$) | Li | >70 |
| DVBS-Na | — | — | — | — | — | 8 |

In separate experiments from those shown in Table 4 and for comparison, the highest solubility achieved by combining lithium styrene sulphonate (LiSS) and DVBS-Na was 55 wt % whereas when such monomers (e.g. LiSS and NaSS) were combined with the compounds of Formula (I), compositions were achieved with solid contents of more 70 wt %.

ER (ohm·$cm^2$) of the polymer films prepared in the Examples was measured by the method described by Dlugolecki et al., J. of Membrane Science, 319 (2008) on page 217-218 with the following modifications:

- the auxiliary membranes were CMX and AMX from Tokuyama Soda, Japan;
- the capillaries as well as the Ag/AgCl references electrodes (Metrohm type 6.0750.100) contained 3M KCl;
- the calibration liquid and the liquid in compartment 2, 3, 4 and 5 was 0.5 M NaCl solution at 25° C.;
- the effective polymer film area was 9.62 $cm^2$;
- the distance between the capillaries was 5.0 mm;
- the measuring temperature was 25° C.;
- a Cole Parmer Masterflex console drive (77521-47) with easy load II model 77200-62 gear pumps was used for all compartments;
- the flowrate of each stream was 475 ml/min controlled by Porter Instrument flowmeters (type 150AV-B250-4RVS) and Cole Parmer flowmeters (type G-30217-90); and
- the samples of polymer film were equilibrated for at least 1 hour at room temperature in a 0.5 M solution of NaCl prior to measurement.

Preferably, the ER (for 0.5 M NaCl) is lower than 5 ohm·$cm^2$, more preferably lower than 2.5 ohm·$cm^2$.

Measurement of Permselectivity (PS)

The permselectivity PS (%) that is the selectivity to the passage of ions of opposite charge to that of the polymer films prepared in the examples, was measured as follows. The polymer film to be analysed was placed in a two-compartment system. One compartment is filled with a 0.05M solution of NaOH and the other with a 0.5M solution of NaOH.

Settings:

- the capillaries as well as the Ag/AgCl reference electrodes (Metrohm type 6.0750.100) contained 3M KCl;
- the effective polymer film area was 9.62 $cm^2$;
- the distance between the capillaries was ca 15 mm;
- the measuring temperature was 21.0±0.2° C.;
- a Cole Parmer Masterflex console drive (77521-47) with easy load II model 77200-62 gear pumps was used for the two compartments;
- Porter Instrument flowmeters (type 150AV-B250-4RVS) and Cole Parmer flowmeters (type G-30217-90) were used to control the flow constant at 500 ml/min;
- The samples of polymer film were equilibrated for 1 hr in a 0.5M NaOH solution prior to measurement. The voltage was read from a regular VOM (multitester) after 20 minutes.

Preferably the PS for NaOH is at least 50%.

pH Stability

Stability in acidic and/or alkaline conditions is preferred as it widens the scope of applications the polymer films can be used in. Stability is typically tested by immersing samples of the polymer film under evaluation in 4M of HCl or NaOH at 80 degrees for 7 days. After this treatment, the selectivity of the polymer film should be at least 80% of the original selectivity to be judged as stable.

Extraction Analysis

In order to analyse the polymerisation degree of polymer films and show the presence of the claimed materials in polymer films, samples of the polymer films were extracted with purified water (10 $cm^2$ in 50 mL purified water) after which the extraction liquid was analysed using the HPLC-MS method described above

Preparation of Compounds of Formula (I) and Comparative Compound

Synthesis of Starting Materials

Cl-SS

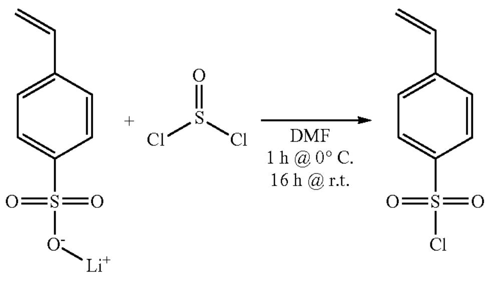

Thionyl chloride (109 mL, 178.46 g, 1.5 mol, 3 moleq) was added dropwise to a solution of 4-vinylbenzenesulfonic acid lithium salt (95.08 g, 0.500 mol, 1 moleq) and 4OH-TEMPO (50 mg, 500 ppm) in DMF (300 mL) in a double-walled reactor that was actively cooled to 5° C. After the addition was completed, the solution was allowed to slowly heat to room temperature and was stirred for another 16 hours. Then the reaction mixture was poured into 1 liter of cold 1M KCl in a separation funnel. The bottom layer was removed and dissolved in 500 mL diethylether. This solution was washed with a 1M KCl-solution (300 mL). The organic layer was dried over sodium sulfate, filtered and concentrated in vacuum to give a yellow oil. The crude product was used without further purification in the next step. Typical yield was 89.5 g (88%). HPLC-MS purity>98%; $^1$H-NMR: <2 wt % DMF, 0% diethyl ether.

Cl-DVBS

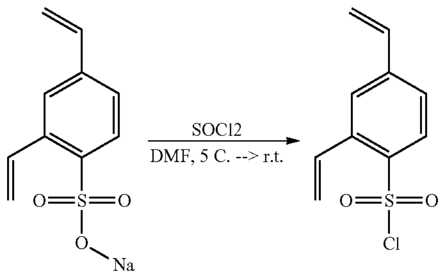

Thionyl chloride (75 mL, 123.1 g, 1.034 mol, 3 moleq) was added dropwise to an solution of divinylbenzene sulfonate sodium salt (80 g, 0.345 mol, 1 moleq) and 4OH-TEMPO (50 mg, 500 ppm) in DMF (300 mL) in a double-walled reactor that was actively cooled to 5° C. After the addition was completed, the solution was allowed to slowly heat to room temperature and was stirred for another 16 hours. Then the reaction mixture was poured into 1 liter of cold 1M KCl in a separation funnel. The bottom layer was removed and dissolved in 500 mL diethylether. This solution was washed with a 1M KCl-solution (300 mL). The organic layer was dried over sodium sulfate, filtered and concentrated in vacuo to give a yellow oil. The crude product was used without further purification in the next step. Typical yield was 62 g (79%). HPLC-MS purity>98%; $^1$H-NMR:<2 wt % DMF, 0% diethyl ether.

NH2-SS

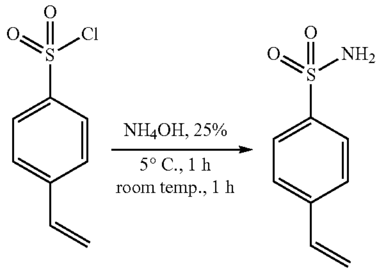

NH2-SS

Thionyl chloride (109 mL, 178.46 g, 1.5 mol, 3 moleq) was added dropwise to a solution of 4-vinylbenzene-sulfonic acid lithium salt (95.08 g, 0.500 mol, 1 moleq) and 4OH-TEMPO (50 mg, 500 ppm) in DMF (300 mL) in a double-walled reactor that was actively cooled to 5° C. After the addition was completed, the solution was allowed to slowly heat to room temperature and was stirred for another 16 hours. Then the reaction mixture was poured into 1 liter of cold 1M KCl in a separation funnel. The bottom layer was removed and was added dropwise to a solution of ammonium hydroxide 25% in water (250 mL, 3.67 mol, 15 moleq) and 4OH-TEMPO (50 mg, 500 ppm) in a double-walled reactor that was actively cooled to 5° C. After the addition was completed, the solution was stirred for 1 hour. The solution was then allowed to heat to room temperature and was stirred for one hour.

Then the reaction mixture was cooled back to 5° C. and the product was filtered off and washed with 50 mL of cold water. The product was dried overnight in vacuum at 30° C. and used without further purification. Typical yield was 66.8 g (73%). HPLC-MS purity>95%.

Synthesis of Compounds of Formula (I)

Example 1—XL-D

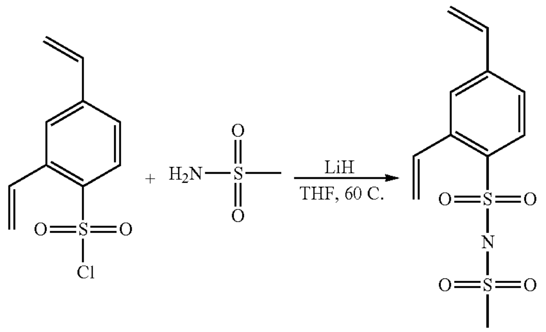

Before the synthesis, methane sulfonamide was dried in a vacuum oven overnight (30° C., vac). To a solution of the dried methane sulfonamide (8.32 g, 0.087 mol, 1 moleq) and 4OH-TEMPO (30 mg, 500 ppm) in THF (100 mL) was added LiH (1.53 g, 0.192 mol, 2.2 moleq) as a solid at once. The reaction mixture was stirred for 30 minutes at room temperature. Then, a solution of Cl-DVBS (20 g, 0.087 mol, 1 moleq) in THF (50 mL) was added to the reaction mixture. After addition, the reaction mixture was heated to 60° C. (water bath temperature). After two days, the reaction mixture was filtrated over celite to remove the excess of LiH. The filtrate was concentrated in vacuo to give a light yellow foam. The resulting foam was dissolved in 500 mL ethyl acetate. Celite was added and the resulting slurry was stirred for 5 minutes. Then, the celite was filtered off and washed with 100 mL ethyl acetate. This Celite procedure was then repeated. The solvent was then evaporated in vacuo and the resulting white foam was washed with 500 mL diethyl ether overnight. The resulting white powder was filtered off and dried in a vacuum oven at 30° C. for 16 h yielding a hygroscopic white solid. Typical achieved yield wa 15.5 g (60%). HPLC-MS purity>95%; $^1$H-NMR:<3 wt % residual solvents; 2 wt % divinylbenzene sulfonate; ICP-OES: 24-30 g Li/kg product.

Example 2—XL-B

Before the synthesis, benzene sulfonamide was dried in a vacuum oven overnight (30° C., vac). To a solution of the dried benzene sulfonamide (11.12 g, 0.061 mol, 1 moleq) and 4OH-TEMPO (30 mg, 500 ppm) in THF (100 mL) was added LiH (1.06 g, 0.134 mol, 2.2 moleq) as a solid at once. The reaction mixture was stirred for 30 minutes at room temperature. Then, a solution of Cl—SS (12.3 g, 0.061 mol, 1 moleq) in THF (50 mL) was added to the reaction mixture. After

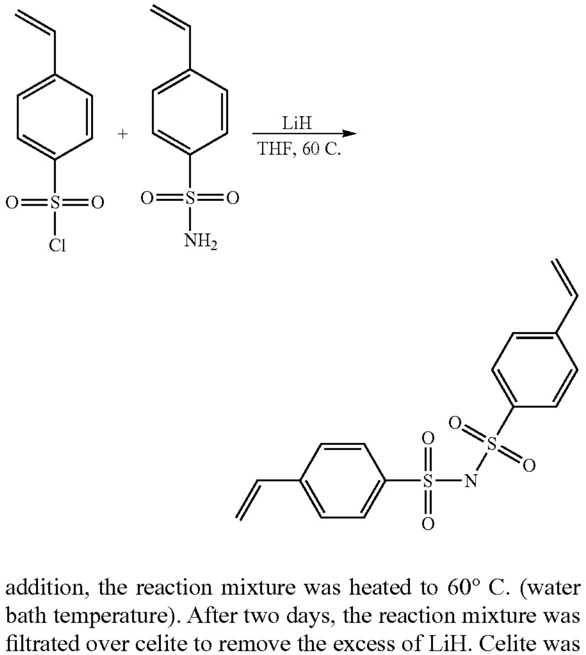

addition, the reaction mixture was heated to 60° C. (water bath temperature). After two days, the reaction mixture was filtrated over celite to remove the excess of LiH. Celite was added and the resulting slurry was stirred for 5 minutes. Then, the celite was filtered off and washed with 100 mL ethyl acetate. The solvent was then evaporated in vacuo and the resulting white foam was washed with 500 mL diethyl ether overnight. The resulting white powder was filtered off and dried in a vacuum oven at 30° C. for 16 h yielding a white solid. Typical yield was 11 g (51%). HPLC-MS purity>94%; $^{1}$H-NMR:<1 wt % residual solvents, <5 wt % styrene sulfonate or styrene sulfonamide; ICP-OES: 21-26 g Li/kg product.

Example 3—XL-2

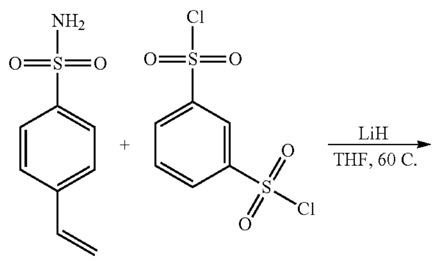

-continued

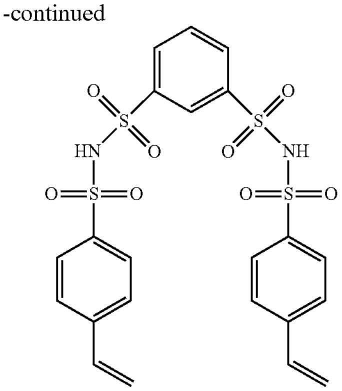

Before the synthesis, styrene sulfonamide was dried in a vacuum oven overnight (30° C., vac). To a solution of the dried styrene sulfonamide (16.90 g, 0.092 mol, 2.05 moleq) and 4OH-TEMPO (30 mg, 500 ppm) in THF (100 mL) was added LiH (1.50 g, 0.189 mol, 4.2 moleq) as a solid at once. The reaction mixture was stirred for 30 minutes at room temperature. Then, a solution of 1,3 benzene disulfonyl chloride (12.38 g, 0.045 mol, 1 moleq) in THF (50 mL) was added to the reaction mixture. After addition, the reaction mixture was heated to 60° C. (water bath temperature). After 2 days, the reaction mixture was filtrated over celite to remove the excess of LiH. The filtrate was concentrated in vacuo to give a light yellow foam. The resulting foam was dissolved in 500 mL ethyl acetate. Celite was added and the resulting slurry was stirred for 5 minutes. Then, the celite was filtered off and washed with 100 mL ethyl acetate. This Celite procedure was then repeated. The solvent was then evaporated in vacuo and the resulting white foam was washed with 500 mL diethyl ether overnight. The resulting white powder was filtered off and dried in a vacuum oven at 30° C. for 16 h yielding a hygroscopic white solid. Typical achieved yield was 14.5 g (54%). HPLC-MS purity>96%; $^{1}$H-NMR:<2 wt % residual solvents; <2 wt % styrene sulfonamide; ICP-OES: 35-40 g Li/kg product.

Example 4—XL-SAS

Step 1

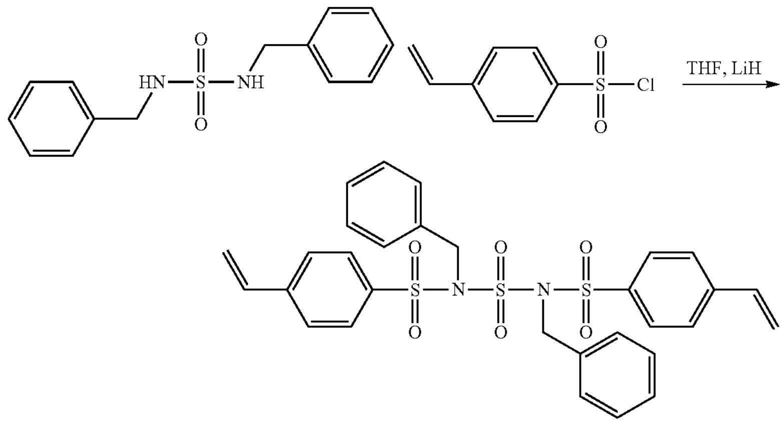

To a solution of bisbenzylsulfonamide in THF LiH was added. The reaction mixture was stirred for 15 minutes. Then vinylbenzenesulfonylchloride was added at once and the reaction mixture was heated to 50° C. After 20 h at 50° C. the reaction mixture was cooled down to room temperature, filtered and the residue was washed with THF. The filtrate was concentrated in vacuo. The resulting solid was stirred in ether, and filtered again. The filtrate was concentrated in vacuo and purified by column chromatography.

Step 2

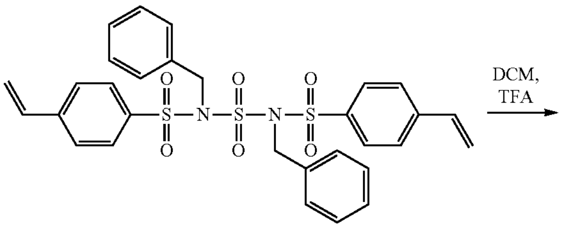

-continued

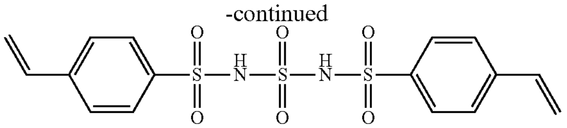

The benzylprotected LiBVBSAS was dissolved in DCM and TFA, and stirred overnight at room temperature. The product was filtered off, dried in vacuum and isolated as a white solid. Typical yield of the two steps was 45%, HPLC-MS purity>96%; $^1$H-NMR:<2 wt % residual solvents; <2 wt % styrene sulfonamide; ICP-OES: 35-40 g Li/kg product.

Preparation of Component (b)

MM-Tf, MM-A, MM-P and MM-M (referred to above) had the structures shown below.

MM-Tf

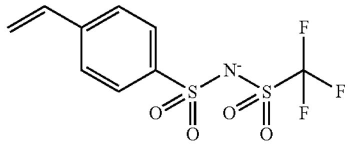

MM-A

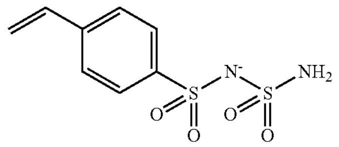

MM-P

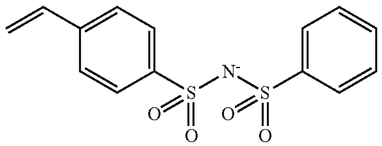

MM-M

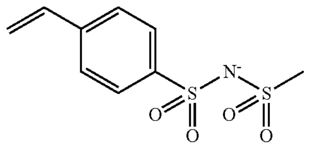

The compounds MM-Tf, MM-A, MM-P and MM-M were synthesized according to the following general scheme and procedure:

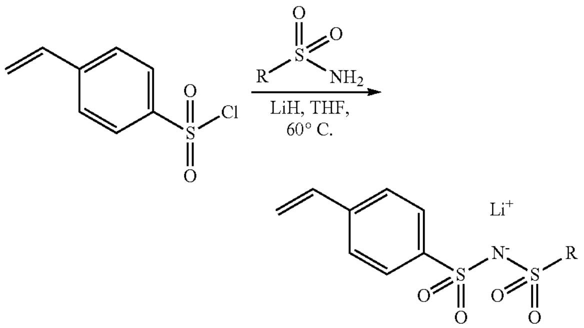

R = —$CH_3$, —$CF_3$, —Ph, —$NH_2$

General Procedure

Before the synthesis, the corresponding sulfamide was dried in a vacuum oven overnight at 30° C. To a solution of the dried sulfamide (0.100 mol, 1 moleq) and 4OH-TEMPO (30 mg, 500 ppm) in THF (100 mL) was added LiH (0.300 mol, 3 moleq) as a solid at once. The reaction mixture was stirred for 30 minutes at room temperature. Then, a solution of vinyl benzyl sulphonyl chloride (0.100 mol, 1 moleq) in THF (50 mL) was added and the reaction mixture was heated to 60° C. (water bath temperature) for 16 h. The resulting solution was filtrated over celite and the resulting foam was dissolved in 500 mL ethyl acetate. Celite was added and the resulting slurry was stirred for 5 minutes. Then, the celite was filtered off and washed with 100 mL ethyl acetate. The solvent was then evaporated in vacuum and the resulting white foam was crushed with 500 mL diethyl ether overnight. The resultant compound of Formula (b) was collected by filtration and isolated as a white hygroscopic powder. Data on yield and purity are given in Table 5 below.

TABLE 5

Compounds of Formula (b) and comparative compound

| R | Yield | Purity | Residual solvent | Residual LiSS | Li content |
|---|---|---|---|---|---|
| methyl | 80% | >94% | <1% | <4% | 26-30 g/kg |
| phenyl | 79% | >96% | <1% | <2% | 23-28 g/kg |
| trifluoromethyl | 70% | 81% | 17% | | |
| amino | 63% | >92% | <1% | <6% | 26-40 g/kg |

Composition Examples 1 to 11, Comparative Examples CEx1 to CEx5 and Polymer Films Table 6 below describes compositions of Examples 1 to 11 according to the second aspect of the present invention and Comparative Examples CEx1 to CEx5. Each of the compositions was polymerised to form a polymer film of thickness 100 μm by coating the compositions described in Table 6 below onto PP/PE Support for reinforcement with the aid of a 100 μm Meyer bar. The electrical resistance (ER) of the resultant polymer films was measured using 0.5N NaCl, the permselectivity (PS) was measured as described above and the result is shown in Table 7 below. The pH of the resultant polymer films were measured by the method described above and the results are also shown in Table 7 below.

TABLE 6

| Compositions | | | | | | | | | | |
|---|---|---|---|---|---|---|---|---|---|---|
| | Components and their amount in the composition | | | | | | | | | |
| Example | (b) | (b) (wt %) | (b) (M) | (a) | (a) (wt %) | (a) (M) | (c) | (c) (wt %) | (d) (LAP) (wt %) | Molar fraction (a) |
| Ex.1 | MM-M | 25 | 0.94 | XL-2 | 35 | 0.60 | water/1 MP | 29/10 | 1 | 0.39 |
| Ex.2 | none | 0 | 0 | XL-2 | 60 | 1.03 | Water/1 MP | 29/10 | 1 | 1.0 |
| Ex.3 | none | 0 | 0 | XL-D | 60 | 2.05 | MeOH | 38 | 2 | 1.0 |
| Ex.4 | none | 0 | 0 | XL-D | 66 | 2.25 | MeOH | 32 | 2 | 1.0 |
| Ex.5 | none | 0 | 0 | XL-2 | 66 | 1.14 | water/IPA/1 MP | 20.5/3.5/9 | 1 | 1.0 |
| Ex.6 | none | 0 | 0 | XL-2 | 67 | 1.15 | water/IPA/1 MP | 20.5/3.5/8 | 1 | 1.0 |
| Ex.7 | MM-M | 12 | 0.45 | XL-D | 54 | 1.84 | water/MCH/1 MP | 20.5/3.5/9 | 1 | 0.80 |
| Ex.8 | MM-M | 25 | 0.94 | XL-B | 35 | 0.99 | Water/DMSO/IPA/1 MP | 19.3/6.4/3.3/10 | 1 | 0.51 |
| Ex.9 | MM-M | 19 | 0.71 | XL-2 | 41 | 0.71 | Water/IPA/1 MP | 24.9/4.1/10 | 1 | 0.50 |
| Ex.10 | MM-P | 34 | 1.03 | XL-B | 36 | 1.01 | Water/TEOA | 26/3 | 1 | 0.50 |
| Ex. 11 | MM-A | 30 | 1.12 | XL-B | 40 | 1.13 | Water/TEOA | 26/3 | 1 | 0.50 |
| CEx1 | LiSS | 36 | 1.89 | Na-DVBS | 20 | 0.86 | Water/TEOA | 39.5/3.5 | 1 | 0.31 |
| CEx2 | LiSS | 26 | 1.37 | XL-2 | 31 | 0.53 | Water/TEOA | 38/4 | 1 | 0.28 |
| CEx3 | MM-tF | 39 | 1.21 | XL-B | 31 | 0.87 | Water/TEOA | 26/3 | 1 | 0.42 |
| CEx4 | Na-AMPS | 30 | 1.31 | M-11 | 30 | 0.60 | Water | 39 | 1 | 0.31 |
| CEx.5 | Mm-M | 41 | 1.53 | XL-2 | 19 | 0.33 | Water/IPA/1 MP | 24.9/4.1/10 | 1 | 0.18 |

Na-AMPS amount in the Table is based on Na-AMPS being 100% solids. The water content of Na-AMPS (as provided by the supplier) was included in the amount of component (c).
M means mol per kg.

TABLE 7

| ER, PS and pH stability of the polymer films | | | | |
|---|---|---|---|---|
| Example | ER (ohm · $cm^2$) (0.5N NaCl) | PS (%) (0.05/0.5N NaOH) | PS after 7 days 4M HCl @ 80° C. (%) (0.05/0.5N NaOH) | PS after 7 days 4M NaOH @ 80° C. (%) (0.05/0.5N NaOH) |
| Ex 1 | 1.2 | 52 | 51 | 50 |
| Ex 2 | 1.5 | 64 | 63 | 64 |
| Ex 3 | 1.4 | 51 | 52 | 53 |
| Ex 4 | 1.4 | 58 | 57 | 56 |
| Ex 5 | 1.9 | 57 | 57 | 58 |
| Ex 6 | 1.8 | 70 | 69 | 72 |
| Ex 7 | 1.5 | 52 | 53 | 51 |
| Ex 8 | 1.5 | 50 | 51 | 50 |
| Ex 9 | 1.16 | 61 | 59 | 61 |
| Ex 10 | 1.3 | 60 | 58 | 59 |
| Ex 11 | 1.4 | 55 | 55 | 56 |
| CEx 1 | 1.1 | 25 | n.m. | n.m |
| CEx 2 | 0.94 | 26 | n.m. | n.m |
| CEx 3 | 0.87 | 0 | n.m. | n.m |
| CEx 4 | 2.5 | 60 | 0 | 0 |
| CEx. 5 | 0.7 | 12 | n.m. | n.m. |

n.m. means not measured

Extraction Analysis

The results of the extraction analysis described above are shown in Table 8 below.

TABLE 8

| Extraction results | | | | |
|---|---|---|---|---|
| Example | Material (a) | Extracted material (a) (mg/ml) | Material (b) | Extracted material (b) (mg/ml) |
| Ex 8 | MM-M | 13 | XL-B | 8 |
| Ex 10 | MM-P | 12 | XL-B | 9 |
| Ex 1 | MM-M | 14 | XL-2 | 11 |
| Ex 11 | MM-A | 18 | XL-B | 15 |

Preparation of the AEL

An AEL composition was prepared containing N,N,N',N'-tetramethyldiaminopropane, 1,4-bis[(4-ethenylphenyl) methyl]-, chloride (46.1 wt %), 4-Vinylbenzyl trimethylammonium chloride (23 wt %), water (28 wt %), 4-hydroxy TEMPO (2 wt %), and Omnirad™ 1173 (0.9 wt %). The AEL composition was coated onto PE Support and cured by UV to give an AEL.

Preparation of the CEL and Application to the AEL to Produce a BPM

The CEL compositions described in Table 7 were prepared (Example 9 & Comparative Example CEx4) and were coated on the AEL prepared as described above, then a second piece of PE Support was placed onto the layer of CEL composition, Excess CEL composition was wiped-off and the CEL composition was cured using UV light to give BPMs.

The electrochemical properties and bipolar characteristics of the BPMs so prepared were compared to a reference bipolar membrane (Fumasep from Fumatech) using a so-called Current-Voltage characteristic (I-U curve), where the current density was measured as a function of the applied voltage. Typically, a low voltage (U) required to generate a given current density, i.e. 600 mA/$cm^2$ indicates that one or both of the AEL and CEL and also the BPM have a low ionic resistance. Low ionic resistance, in this case of the CEL, results in membranes that are more energy efficient. The results for Example 9 and comparative Example CEx4 are shown in Table 9 below.

TABLE 9

| ER of CEL and voltage U of BPM at 600 mA/$cm^2$ | | |
|---|---|---|
| Example | ER of CEL (ohm/$cm^2$) | U @ 600 mA/$cm^2$ of BPM (Volt) |
| Ex 9 | 1.3 | 3.8 |
| CEx 4 | 2.5 | 5.5 |

The invention claimed is:

1. A polymer film obtainable by curing a composition comprising a compound of Formula (I):

Formula (I)

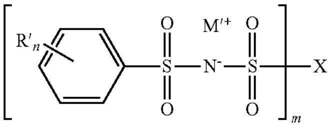

wherein:

R' is vinyl, epoxy or $C_{1-3}$-alkylenethiol:

n has a value of 1 or 2;

m has a value of 1, 2 or 3;

$M'^+$ is a cation;

wherein:

(i) when m and n both have a value of 1 then X is vinylphenyl or of Formula (II):

Formula (II)

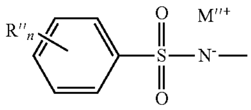

wherein in Formula (II):

R" is vinyl, epoxy or $C_{1-3}$-alkylenethiol;

$M''^+$ is a cation; and n in Formula (II) has a value of 1 or 2;

(ii) when m has a value of 2 or 3 then X is $C_{1-6}$-alkylene, $C_{6-18}$-arylene, or $N(R''')_{(3-m)}$ wherein each R''' independently is H or $C_{1-4}$ alkyl; and (iii) when m has a value of 1 and n shown in Formula (I) has a value of 2 then X is of Formula (II) (as defined above) or $C_{1-6}$-alkyl, $C_{6-18}$-aryl, or $N(R''')_2$ wherein each R''' independently is H or $C_{1-4}$ alkyl;

wherein the molar fraction of the compound of Formula (I) in relation to all curable compounds in the composition is greater than 0.25.

2. The polymer film according to claim 1 wherein n shown in Formula (I) has a value of 1 and m has a value of 2.

3. The polymer film according to claim 1 wherein the composition further comprises a compound comprising one and only one polymerisable group and a bissulfonylimide group.

4. The polymer film according to claim 1 wherein the composition comprises the following ingredients:

(a) a compound of Formula (I);

optionally (b) a compound comprising one and only one polymerisable group;

optionally (c) a solvent; and optionally (d) a radical initiator.

5. The polymer film according to claim 1 which comprises:

(a) 20 to 80 wt % of component (a);

(b) 0 to 50 wt % of component (b);

(c) 10 to 40 wt % of component (c); and (d) 0 to 10 wt % of component (d).

6. The polymer film according to claim 1 which is a cation exchange membrane.

7. A bipolar membrane comprising the polymer film according to claim 1.

8. The polymer film according to claim 1 which further comprises a porous support.

9. A method of using the polymer film according to claim 6 for the treatment of polar liquids, for the generation of hydrogen or for the generation of electricity.

10. A method of using the bipolar membrane according to claim 7 for production the acids and bases, for the separation and treatment of organic acids or for the generation of electricity.

11. The polymer film according to claim 1 wherein the composition comprises 20 to 80 wt % of the compound of Formula (I).

12. The polymer film according to claim 1 wherein the molar fraction of the compound of Formula (I) in relation to all curable compounds in the composition is greater than 0.30.

13. The polymer film according to claim 1 being free from perfluoro-groups.

14. The polymer film according to claim 1 wherein $M'^+$ and $M''^+$ are independently selected from $H^+$, $Li^+$, $Na^+$, $K^+$ or $NL_4^+$ wherein each L independently is H or $C_{1-3}$-alkyl.

15. The polymer film according to claim 3 wherein said compound comprises a compound of Formula (III):

Formula (III)

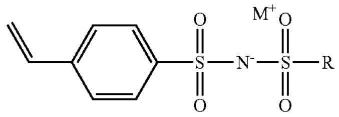

wherein

R is $C_1$-$C_4$ alkyl, $NH_2$, $C_6$-$C_{12}$ aryl; and $M^+$ is $H^+$, $Li^+$, $Na^+$, $K^+$, $NL_4^+$ wherein L is H or $C_1$-$C_3$ alkyl.

16. The polymer film according to claim 1 wherein (i) the composition comprises 20 to 80 wt % of the compound of Formula (I);

(ii) the molar fraction of the compound of Formula (I) in relation to all curable compounds in the composition is greater than 0.30; and (iii) polymer film is free from perfluoro-groups.

17. The polymer film according to claim 16 wherein the composition further comprises a compound comprising one and only one polymerisable group and a bissulfonylimide group.

18. The polymer film according to claim 17 wherein n shown in Formula (I) has a value of 1 and m has a value of 2.

* * * * *